(12) United States Patent
Robinson

(10) Patent No.: US 6,393,095 B1
(45) Date of Patent: May 21, 2002

(54) AUTOMATIC DEFECT DETECTION

(75) Inventor: Max Robinson, Nottingham (GB)

(73) Assignee: The Nottingham Trent University, Nottingham (GB)

( * ) Notice: Subject to any disclaimer, the term of this patent is extended or adjusted under 35 U.S.C. 154(b) by 0 days.

(21) Appl. No.: 09/556,088

(22) Filed: Apr. 21, 2000

(30) Foreign Application Priority Data

Apr. 21, 1999 (GB) .............................................. 9909163

(51) Int. Cl.$^7$ .............................................. G01N 23/18
(52) U.S. Cl. ........................................ 378/58; 378/41
(58) Field of Search ............................... 378/58, 41, 45

(56) References Cited

U.S. PATENT DOCUMENTS

| | | | |
|---|---|---|---|
| 4,475,104 A | 10/1984 | Shen | 340/729 |
| 4,558,359 A | 12/1985 | Kuperman et al. | 358/89 |
| 4,573,191 A | 2/1986 | Kidode et al. | 382/1 |
| 4,598,369 A | 7/1986 | Wang et al. | 364/414 |
| 4,682,160 A | 7/1987 | Beckwith Jr. | 340/729 |
| 4,704,627 A | 11/1987 | Yuyama et al. | 358/88 |
| 4,737,921 A | 4/1988 | Goldwassen et al. | 364/518 |
| 4,837,616 A | 6/1989 | Kasano et al. | 358/107 |
| 4,879,668 A | 11/1989 | Cline et al. | 364/522 |
| 4,985,854 A | 1/1991 | Wittenburg | 364/522 |
| 5,051,904 A | 9/1991 | Griffith | 364/413.16 |
| 5,155,750 A | * 10/1992 | Klynn et al. | 37/42 |
| 5,190,000 A | 3/1993 | Lipton et al. | 358/92 |
| 5,200,819 A | 4/1993 | Nudelman et al. | 358/98 |
| 5,229,935 A | 7/1993 | Yamagishi et al. | 364/413.22 |
| 5,233,639 A | 9/1993 | Marks | 378/42 |
| 6,061,476 A | * 5/2000 | Nichani | 382/270 |

FOREIGN PATENT DOCUMENTS

| | | | |
|---|---|---|---|
| EP | 0 261 984 | 9/1987 | G01N/23/04 |
| EP | 87308517.9 | 9/1987 | G01N/23/04 |
| EP | 0 610 084 B1 | 2/1994 | G06T/15/10 |

OTHER PUBLICATIONS

Negar et al., "Stereo Image Databases for Flight Simulators." Proc. 23$^{rd}$ Southeastern Symposium on System Theory. Mar. 1991, pp. 80–83.

Robinson, et al., "Solid Image Models Derived from Security X–Ray Equipment," European Convention on Security and Detection, 16–18 M16, Conference Publication No. 408, IEE 1995.

* cited by examiner

Primary Examiner—Robert H. Kim
Assistant Examiner—Irakli Kiknadze
(74) Attorney, Agent, or Firm—Fredrikson & Byron, P.A.

(57) ABSTRACT

A pair of stereoscopic images of an object are produced, one image is subtracted from the other, and the resulting two dimensional image is then checked against and compared with a similar two dimensional image (the golden image) which has been produced in an identical manner using a known perfect sample (the golden sample).

7 Claims, 8 Drawing Sheets

Left Perspective  Right Perspective

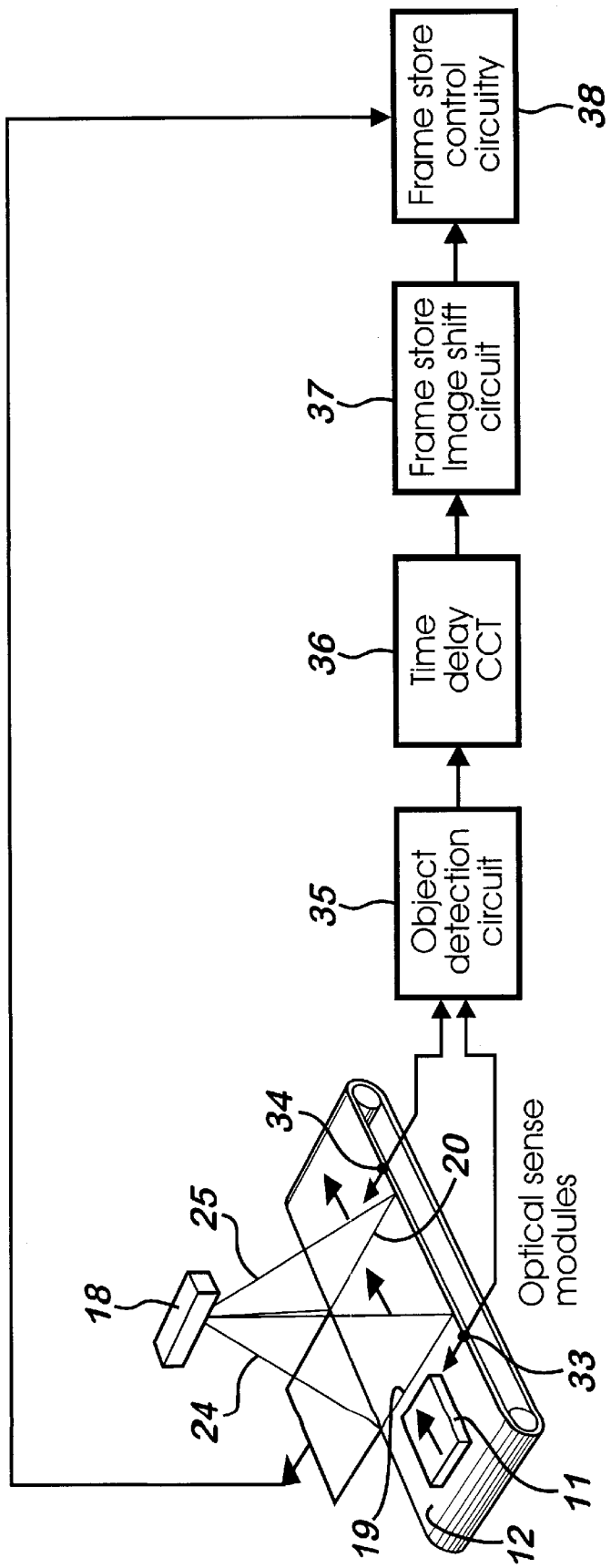

AUTOMATIC DEFECT DETECTION

PRIORITY CLAIM

This application claims priority to British Patent Application No. 9909163.9, filed Apr. 21, 1999.

This invention relates to a method of automatic defect detection for production assemblies.

BACKGROUND TO THE INVENTION

The technique of producing stereoscopic images, whether in visible light or in X-rays, is well known. A stereoscopic image consists of a left and a right perspective view of a given object or scene. When such images are then correctly aligned and presented to a human observer, they provide a full 3-D (binocular stereoscopic) image of the scene.

In general, each of the perspective images contains information taken from slightly different viewpoints. Consequently, the image of a particular feature of an object will be in a slightly different position in each of the perspective views. The physical measurement of this difference is known as binocular parallax or simply parallax.

With stereoscopic images prepared in visual light, a range image can be extracted from the stereoscopic pair if the parallax information is known and the geometrical and optical parameters of the stereoscopic arrangement are also known.

Production of a pair of shadowgraph stereoscopic images using an X-ray source is also known and is described, for example, in European Patent No. 610081. The resulting stereoscopic pair of images can be processed as described in that Patent to produce a 2½D image of an object being viewed.

Whilst, however, such a technique is extremely useful in security situations such as the checking of baggage at airports, such an arrangement does not lend itself to being used to check a production sample against a perfect sample, often known as the "golden sample". Thus, such an arrangement would be very time consuming and would be a processor intensive task. At best, such an arrangement could be used to make random checks rather than to check each production sample and would, therefore, not be a significant improvement over and above typical manual random checks which are made at the moment.

The problem of checking production samples is particularly acute when the production sample involves an electronic assembly. Thus, electronic assemblies are rapidly increasing in complexity whilst, at the same time, decreasing in size. New packaging technologies such as ball grid arrays (devices with their electrical contacts arranged in a dense grid format under the component) and embedded components do not lend themselves to traditional visual inspection techniques since their contacts are both situated under the device and often encapsulated.

An obvious solution and one which has been employed for many years is to employ simple X-ray inspection techniques. However, such simple X-ray inspection techniques do not involve stereoscopic images and only produce a two dimensional shadowgraph. Such shadowgraph images do not contain any depth information and their use is therefore limited.

To overcome this, the object has been manipulated in front of a continuous X-ray source and viewed via a fluorescent screen from many different angles. An operator can then derive his own spacial interpretation of the features and make a decision on the viability of the product. This technique, although versatile, is slow and so is not suitable for in-line inspection and does not lend itself to automation. Also, of course, because the inspection is slow, it would only be possible to examine random production samples rather than to examine all production samples.

It is, therefore, an object of the present invention to provide a detection system which can lend itself to automation and which can be conducted relatively quickly so that all production samples can be checked.

BRIEF SUMMARY OF THE INVENTION

According to the invention, a pair of stereoscopic images of an object are produced, one image is subtracted from the other, and the resulting two dimensional image is then checked against and compared with a similar two dimensional image (the golden image) which has been produced in an identical manner using a known perfect sample (the golden sample).

As a result, the overall three dimensional inspection process is now reduced to a simple comparison of a 2D pattern from the sample under test with the corresponding 2D golden pattern for a known perfect sample. Such a comparison can readily be automated, can be quick and, therefore, is applicable in industrial terms to the checking of each sample on a production line. Thus, for example, the 2D pattern can be considered to be a scanned digital signal and it is relatively simple to compare such a digital signal from one sample with that from the golden sample. If they are identical, then the scanned sample corresponds accurately to the golden sample and if they are not identical then it differs and may therefore be unacceptable as a production product.

Generally speaking, when one is dealing with electronic assemblies, it will be necessary to use X-rays to check the sample since often one will need to view areas which are totally enclosed or encapsulated. In such a case, it is highly convenient that the X-ray images be produced using two parallel curtains of X-rays. The object under test can then be moved on a conveying source such as a conveying belt through and past the two curtains, preferably a pair of diverging thin curtain beams of X-rays, with line detectors beneath the conveying means used to produce the two images. Such a technique is described, for example, in European patent application No. 87308517.9, Serial No. 261 984 and reference is made to that application and its contents are incorporated herein as an example to show how X-ray stereoscopic pairs can be obtained.

The invention, however, is not limited to the use of X-ray images but can just as easily be applied to images produced by visible light or infra-red where only visible surface effects are being checked. Equally, the invention is applicable to ultra-sound images and here, of course, such ultrasound images can be useful in detecting areas which are visually hidden just as with X-rays.

The checking of the golden 2D image pattern relative the 2D image pattern produced from the sample under test can readily be automated by suitable processing techniques. For example, once the two stereoscopic images have been produced, they can be viewed in digital form and one image subtracted from the other to give a resulting digital 2D image. In turn, that resulting digital 2D image can then be checked with the golden 2D image very rapidly by means of a processor and any faults in the original production sample will immediately become apparent because of a mismatch in the two images. On the other hand, if the two images correspond identically, it can be assumed that the sample under test is identical with the golden sample and so the sample under test can be passed as fit for use.

Processors are readily available to conduct this subtraction and compare the resulting 2D pattern with that of the golden image at very high speeds which means that it is then readily possible for one to check the whole of a production output of, say, a mobile telephone production line so that full three dimension external and internal inspection of the manufactured article is possible without the necessity for human intervention.

BRIEF DESCRIPTION OF THE DRAWINGS

The invention will now be illustrated with reference to the accompanying drawings in which some examples of this technique are shown. In the drawings:

FIG. 3 is a diagram illustrating the manner in which the stereoscopic pair of images may be obtained.

DESCRIPTION OF THE PREFERRED EMBODIMENT

Figure 1:
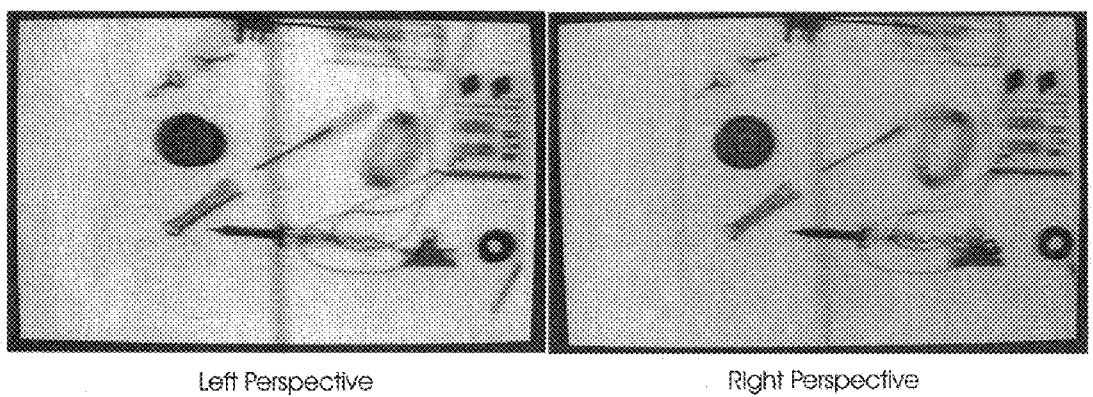
FIG. 1 shows a stereoscopic pair of images obtained by means of x-rays.

Referring now to FIG. 3, a system for obtaining left and right stereoscopic images. The object 11 under test and on the conveyer belt 12 passes successively beneath two collimated curtain beams 24 and 25 from a single X-ray source 18 and over two linescan detector arrays 19 and 20, respectively in the paths of the two beams 24 and 25, which extend transversely of the belt and are spaced in the direction of travel. The passage of the object 11 is sensed by successive optical sensors 33 and 34 which deliver signals to an object detection circuit 35 the output of which is channelled via a time delay circuit 36 and a frame store image shift circuit 37 to frame store control circuitry 38. The linescan information from the two linescan detector arrays 19 and 20 is applied under the control of the frame store control circuitry 38 to respective first and second frame stores 39 and 40 in which the left and right hand stereoscopic images are accumulated and then stored as digital signals.

These signals are then processed by data processing equipment using a program which will subtract one image from the other. This step can be achieved in a conventional manner using image processing programs which are available which have this facility; examples of such commercially available programs are VISILOG from the company known as Noesis and MATROX INSPECTOR from the company known as Matrox.

In FIG. 1, two X-ray images are shown in which are a stereoscopic pair obtained as described above. The left hand picture of FIG. 1 corresponds to the left perspective image and the right hand picture corresponds to the right perspective image.

Figure 2:
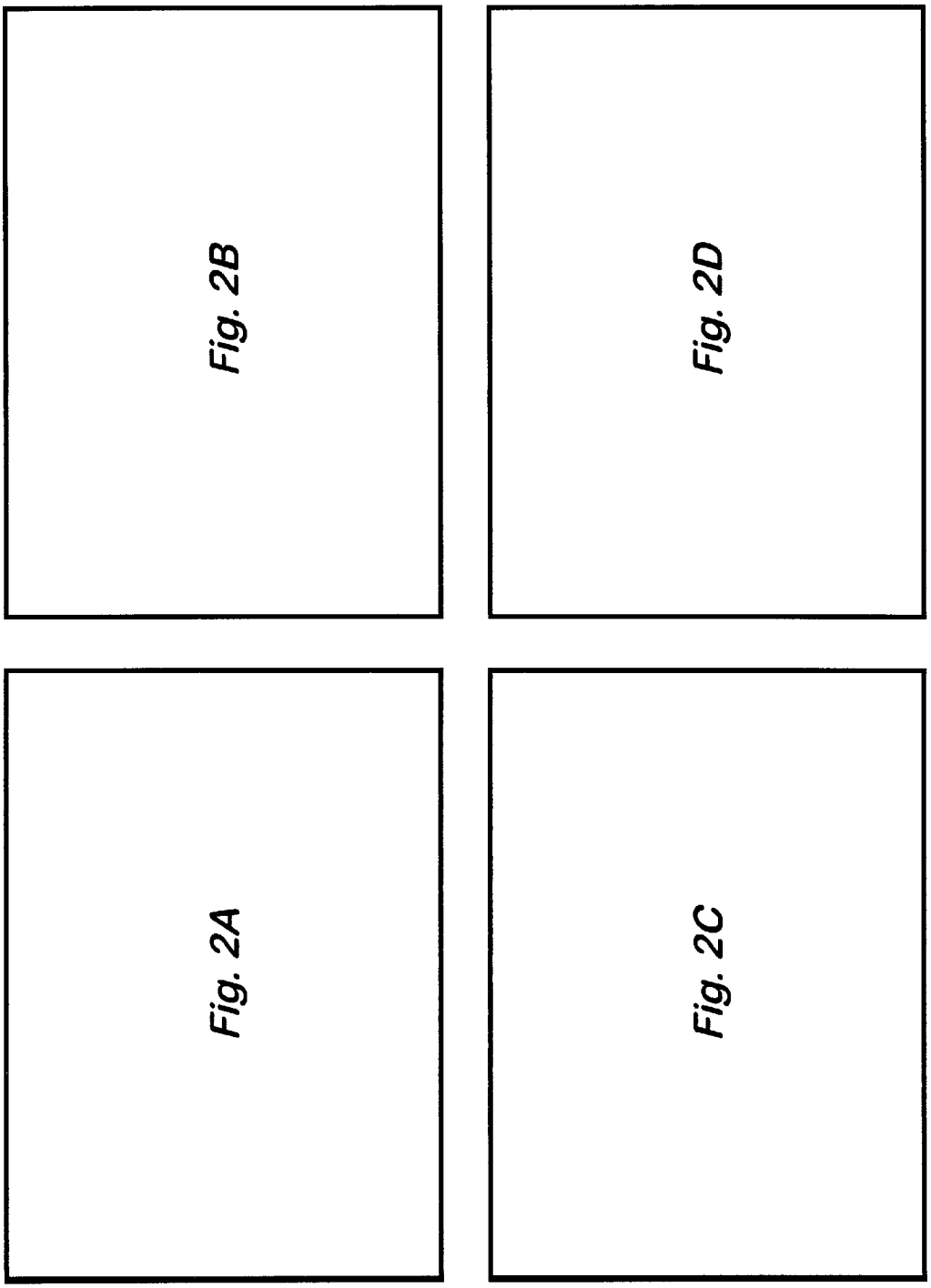
FIG. 2 shows a map of four resulting 2D patterns, which are illustrated in FIGS. 2A–2D, achieved by subtracting one of the pair of images shown in FIG. 1 from the other and four different stereoscopic convergent points.
Figure 2A:
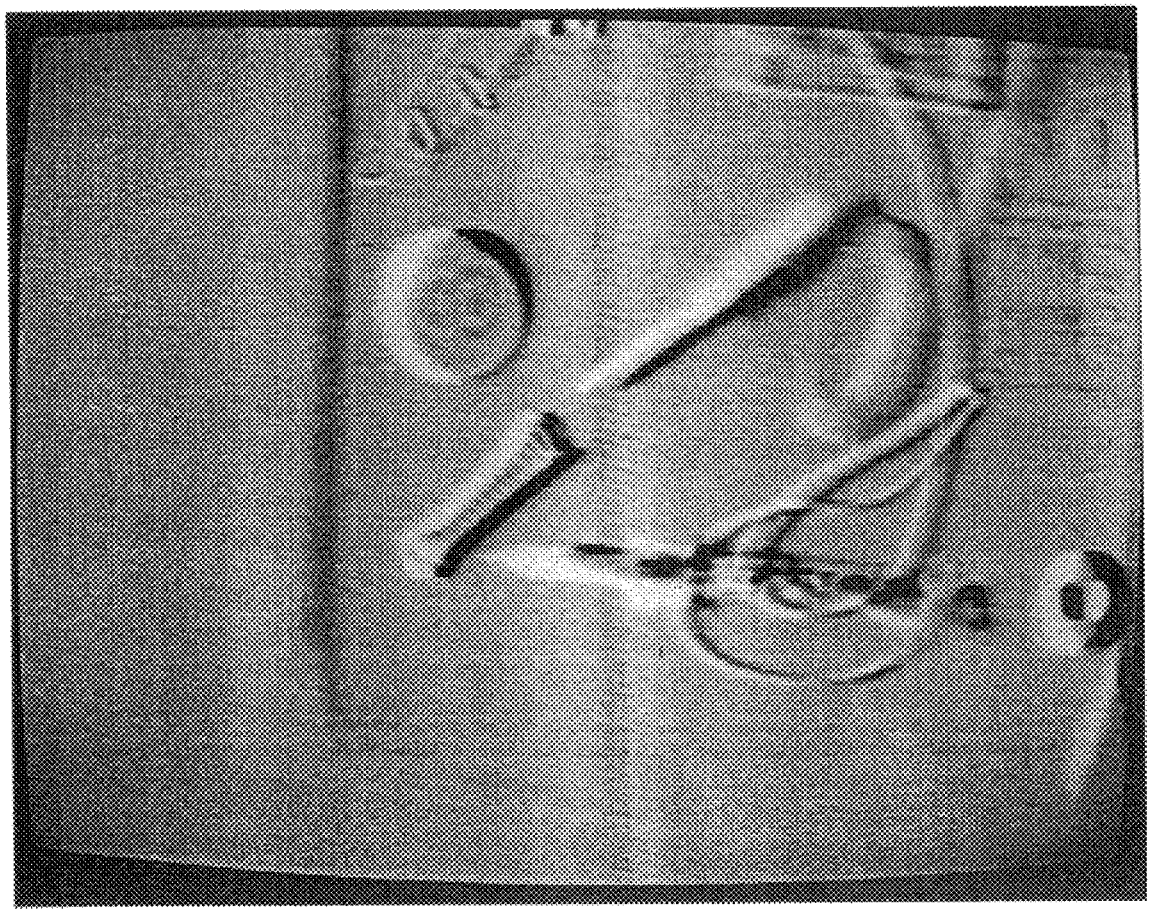
Figure 2B:
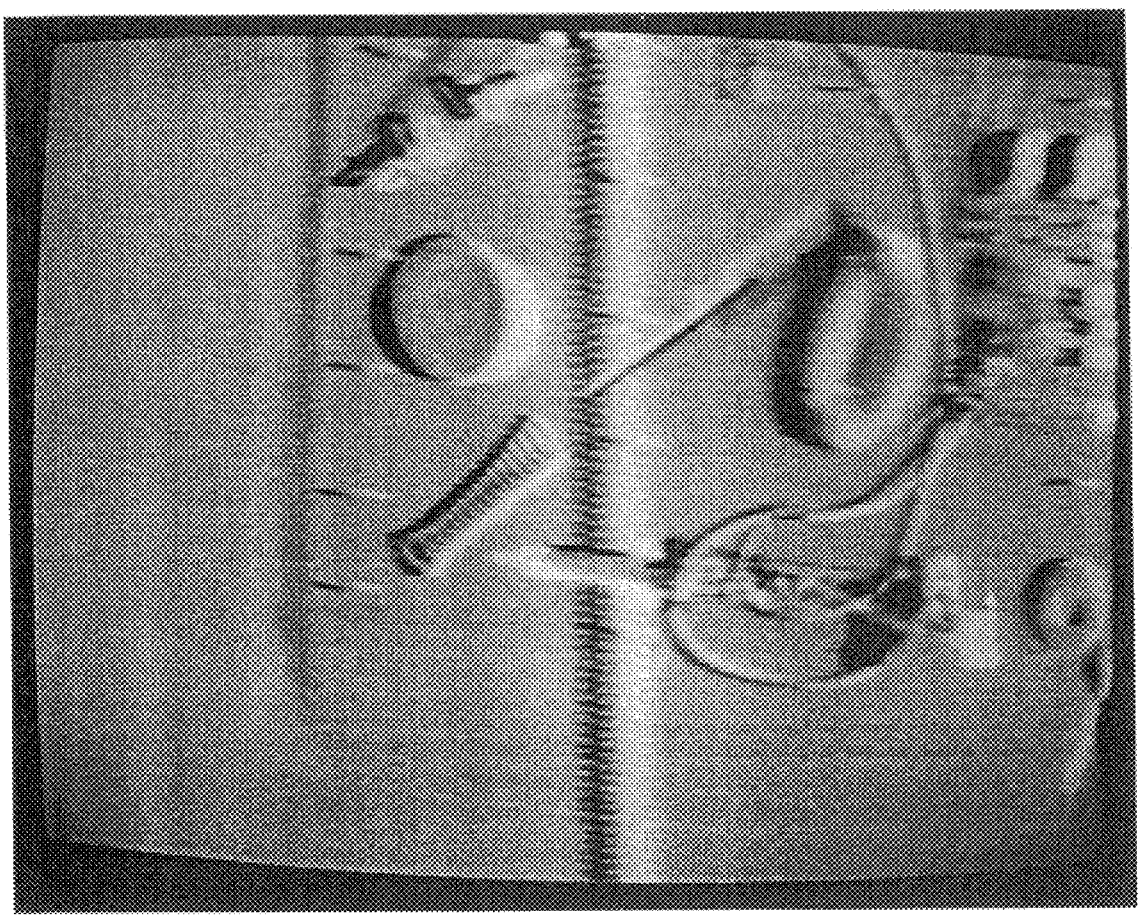
Figure 2C:
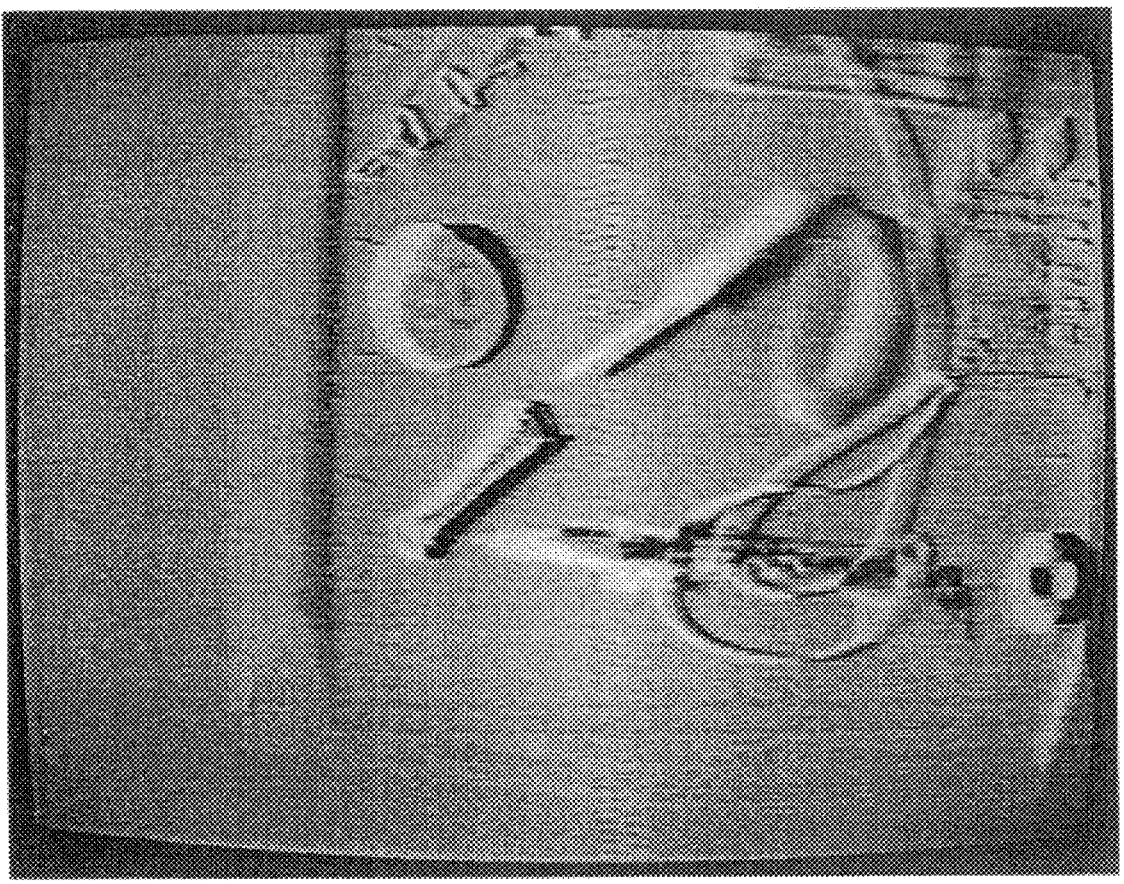
Figure 2D:
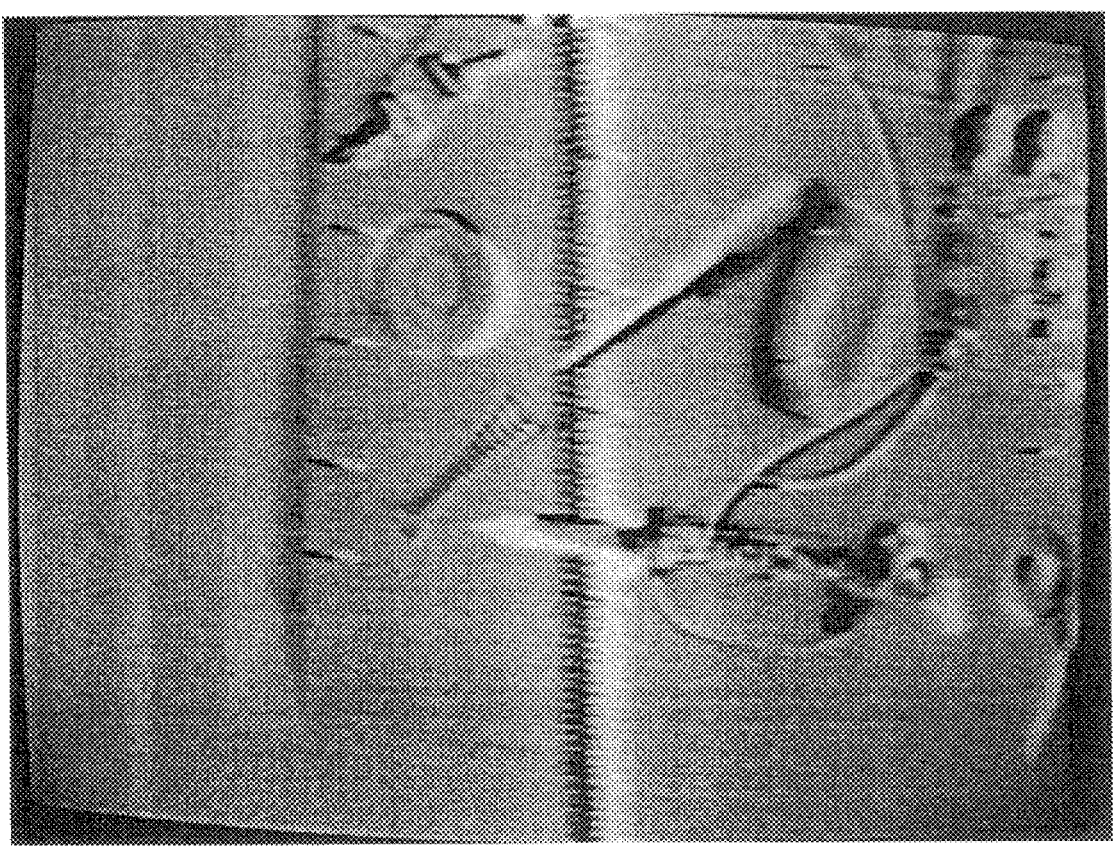
Figure 4:
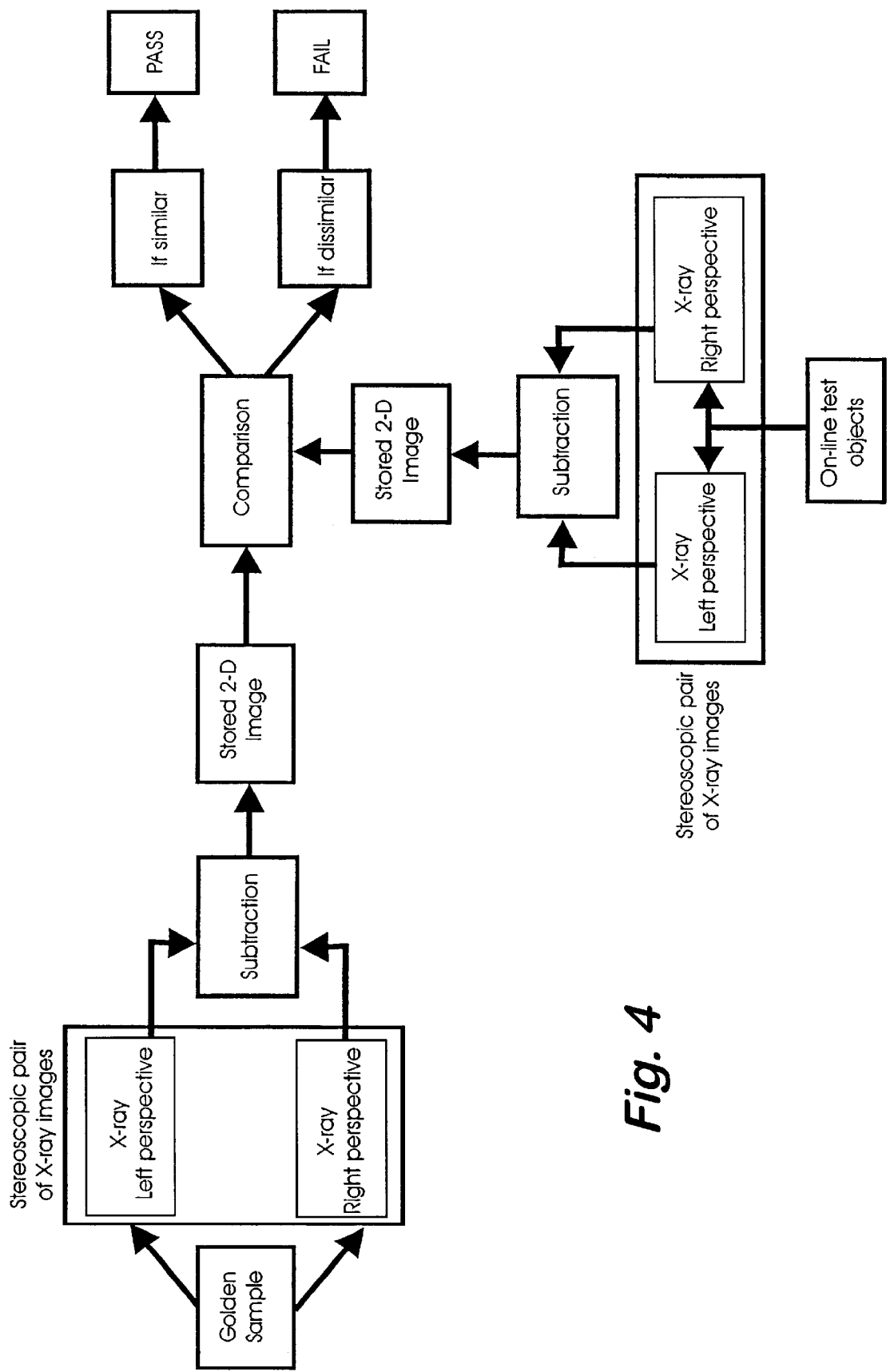
FIG. 4 is a flow chart illustrating the method of the invention.

FIG. 2 maps, and FIGS. 2A–2D show, the results of subtracting the left hand image from the right hand image using different stereoscopic convergent points.

An interesting artifact of these subtracted images is that they appear to be illuminated from the side to the extent of appearing to cast an appropriate shadow. Each of these images, however, as shown in FIG. 1, is a unique subtraction image corresponding to the original sample and that subtraction image can readily and quickly be compared with the corresponding golden subtraction image from a known perfect sample and such subtractions and comparisons can be done by means of suitable software and processors.

An advantage of choosing a particular stereoscopic convergent point is shown by comparing the subtraction images in FIGS. 2A–2D (as mapped in FIG. 2). The object under test was placed on a conveyer belt and it can be seen that imperfections in that conveyor belt, such as the metal links joining the parts of the conveyor belt, are highly visible in the two right hand pictures (FIGS. 2B and 2D) but are almost indistinct in the left hand image. Therefore, according to preferred embodiments of the present invention, one can choose a stereoscopic convergent point which has the effect of removing from the resulting subtracted image as much as possible, if not all, of the background information, such as information concerning the properties of the conveyor or other support on which the item under test has been placed.

While the device of the invention has been specifically described by way of a preferred example, it will be appreciated that changes and modifications may be made therein without departing from the spirit and the scope of the invention as defined in the appended claims.

What is claimed is:

1. A method of detecting a defect in a sample against a golden sample, in which a pair of stereoscopic images of the sample are produced, one image is subtracted from the other to provide a resulting two dimensional image, and that said resulting two dimensional image is checked against a golden two dimensional image which has been produced in identical fashion from the said golden sample, identity of the two images indicating identity between the said sample and the said golden sample, differences indicating a difference between the said sample and the said golden sample.

2. A method as claimed in claim 1 in which the stereoscopic images are X-ray images.

3. A method as claimed in claim 2 further comprising an X-ray source means which directs to X-ray beams through the path of relative movement of the sample to be inspected on to respective line-array detectors situated at the opposite side of the path, the two X-ray beams being set at an angle to one another in the plane containing the path to obtain the left and right perspective views.

4. A method as claimed in claim 3 in which the X-ray source means comprise a single X-ray source and means for deriving therefor two collimated X-ray beams at an angle to one another.

5. A method as claimed in claim 2 in which the sample is moved by conveying means past a pair of X-ray beams.

6. A method as claimed in claim 1 in which the images are obtained or converted to a digital signal and the subtraction and checking steps are performed by subjecting and checking the resulting signals against corresponding golden signals obtained in identical fashion from the said golden sample.

7. A method which forms part of a production process for a product in which the products are conveyed on a conveyor one at a time, each individual product being subjected to a method as claimed in claim 1 where the product is the said sample.

* * * * *